United States Patent
Fyfe et al.

(10) Patent No.: US 7,745,491 B2
(45) Date of Patent: Jun. 29, 2010

(54) SUBSTITUTED PHENYLACETAMIDES AND THEIR USE AS GLUCOKINASE ACTIVATORS

(75) Inventors: Matthew Colin Thor Fyfe, Oxford (GB); Vilasben Kanji Shah, Oxford (GB)

(73) Assignee: Prosidion Limited, Oxford (GB)

( * ) Notice: Subject to any disclaimer, the term of this patent is extended or adjusted under 35 U.S.C. 154(b) by 469 days.

(21) Appl. No.: 11/573,464

(22) PCT Filed: Aug. 9, 2005

(86) PCT No.: PCT/GB2005/050129

§ 371 (c)(1),
(2), (4) Date: Feb. 9, 2007

(87) PCT Pub. No.: WO2006/016194

PCT Pub. Date: Feb. 16, 2006

(65) Prior Publication Data

US 2009/0054444 A1    Feb. 26, 2009

Related U.S. Application Data

(60) Provisional application No. 60/601,078, filed on Aug. 12, 2004.

(51) Int. Cl.
*A61K 31/165* (2006.01)
(52) U.S. Cl. .................. 514/618; 544/224; 544/336; 548/373.1
(58) Field of Classification Search .............. 514/618; 544/224, 336; 548/373.1
See application file for complete search history.

(56) References Cited

U.S. PATENT DOCUMENTS

| | | |
|---|---|---|
| 6,353,111 B1 | 3/2002 | Corbet et al. |
| 6,610,846 B1 | 8/2003 | Bizzarro et al. |
| 7,214,681 B2 | 5/2007 | Fyfe et al. |
| 7,262,196 B2 | 8/2007 | Fyfe et al. |
| 2002/0042512 A1 | 4/2002 | Kester et al. |
| 2002/0198200 A1 | 12/2002 | Kester et al. |
| 2008/0015358 A1 | 1/2008 | Fyfe et al. |
| 2008/0242869 A1 | 10/2008 | Fyfe et al. |
| 2008/0293730 A1 | 11/2008 | Fyfe et al. |
| 2008/0293741 A1 | 11/2008 | Fyfe et al. |
| 2009/0005391 A1 | 1/2009 | Fyfe et al. |

FOREIGN PATENT DOCUMENTS

| | | |
|---|---|---|
| WO | WO 01/85706 A | 11/2001 |
| WO | WO02/46173 | 6/2002 |
| WO | WO 03/095438 A | 11/2003 |
| WO | WO 2004/050645 * | 6/2004 |
| WO | WO 2006/016178 | 2/2006 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Sarabu, R. Expert Opin. Ther. Patents, 18(7), 2008, 759-768.*
Borisy, et al. PNAS, 100(13), 2003, 7977-7982.*
Hackam, et al. JAMA, 296(14), 2006, 1731-1732.*

* cited by examiner

*Primary Examiner*—James O Wilson
*Assistant Examiner*—Douglas M Willis
(74) *Attorney, Agent, or Firm*—James B. Myers

(57) ABSTRACT

Compounds of Formula (I) wherein $R^1$ is a cycloalkylsulphonyl group, or pharmaceutically acceptable salts thereof, are useful in the prophylactic and therapeutic treatment of hyperglycemia and diabetes.

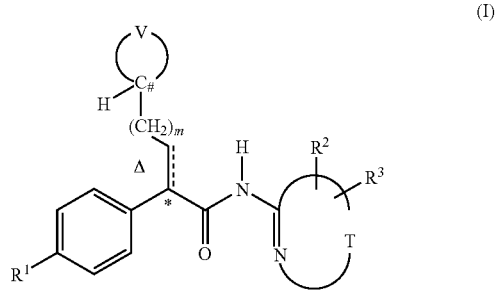

18 Claims, No Drawings

SUBSTITUTED PHENYLACETAMIDES AND THEIR USE AS GLUCOKINASE ACTIVATORS

REFERENCE TO RELATED APPLICATION

This application is submitted as a United States national phase entry, pursuant to 35 USC §371, of PCT/GB2005/050129, filed on 9 Aug. 2005, which claims the benefit of U.S. provisional patent application Ser. No. 60/601,078, filed 12 Aug. 2004, which is incorporated by reference herein.

BACKGROUND OF THE INVENTION

The present invention is directed to tri(cyclo) substituted amide compounds. In particular, the present invention is directed to amide compounds substituted i) at the carbonyl carbon with an ethyl/ethenyl attached to a phenyl ring and a carbocyclic ring, and ii) at the amino with a nitrogen bearing heteroaryl or unsaturated heterocyclyl ring, which are modulators of glucokinase and are useful in the prophylactic or therapeutic treatment of hyperglycemia and diabetes, particularly type II diabetes.

Glucokinase ("GK") is believed to be important in the body's regulation of its plasma glucose level. GK, found principally in the liver and pancreas, is one of four hexokinases that catalyze the initial metabolism of glucose. The GK pathway is saturated at higher glucose levels than the other hexokinase pathways (see R. L. Printz et al., *Annu. Rev. Nutr.*, 13:463-496 (1993)). GK is critical to maintaining the glucose balance in mammals. Animals that do not express GK die soon after birth with diabetes, while animals that overexpress GK have improved glucose tolerance. Activation of GK can lead to hyperinsulinemic hypoglycemia (see, for example, H. B. T. Christesen et al., *Diabetes*, 51:1240-1246 (2002)). Additionally, type II maturity-onset diabetes of the young is caused by the loss of function mutations in the GK gene, suggesting that GK operates as a glucose sensor in humans (Y. Liang et al., *Biochem. J.*, 309:167-173 (1995)). Thus, compounds that activate GK increase the sensitivity of the GK sensory system and would be useful in the treatment of hyperglycemia—particularly the hyperglycemia associated with type II diabetes. It is therefore desirable to provide novel compounds that activate GK to treat diabetes.

International Patent Publication No. WO2001/044216 and U.S. Pat. No. 6,353,111 describe (E)-2,3-disubstituted-N-heteroarylacrylamides as GK activators. International Patent Publication No. WO2002/014312 and U.S. Pat. Nos. 6,369,232, 6,388,088, and 6,441,180 describe tetrazolylphenylacetamide GK activators. International Patent Publication No. WO2000/058293, European Patent Application No. EP 1169312 and U.S. Pat. No. 6,320,050 describe arylcycloalkylpropionamide GK activators. International Patent Publication No. WO2002/008209 and U.S. Pat. No. 6,486,184 describe alpha-acyl and alpha-heteroatom-substituted benzene acetamide GK activators as anti-diabetic agents. International Patent Publication No. WO2001/083478 describes hydantoin-containing GK activators. International Patent Publication No. WO2001/083465 and U.S. Pat. No. 6,388,071 describe alkynylphenyl heteroaromatic GK activators. International Patent Publication No. WO2001/085707 and U.S. Pat. No. 6,489,485 describe para-amine substituted phenylamide GK activators. International Patent Publication No. WO2002/046173 and U.S. Pat. Nos. 6,433,188, 6,441,184, and 6,448,399 describe fused heteroaromatic GK activators. International Patent Publication No. WO2002/048106 and U.S. Pat. No. 6,482,951 describe isoindolin-1-one GK activators. International Patent Publication No. WO2001/085706 describes substituted phenylacetamide GK activators for treating type II diabetes. U.S. Pat. No. 6,384,220 describes para-aryl or heteroaryl substituted phenyl GK activators. French Patent No. 2,834,295 describes methods for the purification and crystal structure of human GK. International Patent Publication No. WO2003/095438 describes N-heteroaryl phenylacetamides and related compounds as GK activators for the treatment of type II diabetes. U.S. Pat. No. 6,610,846 describes the preparation of cycloalkylheteroaryl propionamides as GK activators. International Patent Publication No. WO2003/000262 describes vinyl phenyl GK activators. International Patent Publication No. WO2003/000267 describes aminonicotinate derivatives as GK modulators. International Patent Publication No. WO2003/015774 describes compounds as GK modulators. International Patent Publication No. WO2003047626 describes the use of a GK activator in combination with a glucagon antagonist for treating type II diabetes. International Patent Publication No. WO2003/055482 describes amide derivatives as GK activators. International Patent Publication No. WO2003/080585 describes aminobenzamide derivatives with GK activity for the treatment of diabetes and obesity. International Patent Publication No. WO2003/097824 describes human liver GK crystals and their used for structure-based drug design. International Patent Publication No. WO2004/002481 discloses arylcarbonyl derivatives as GK activators. International Patent Publication Nos. WO2004/072031 and WO2004/072066 (published after the priority date of the present application) disclose tri(cyclo) substituted amide compounds as GK activators.

SUMMARY OF THE INVENTION

Compounds represented by Formula (I):

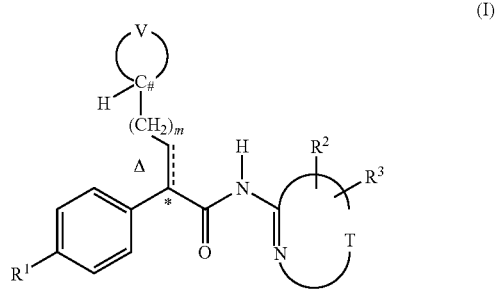

or pharmaceutically acceptable salts thereof, are useful in the prophylactic or therapeutic treatment of hyperglycemia and diabetes, particularly type II diabetes.

DETAILED DESCRIPTION OF THE INVENTION

The present invention is directed to a compound of Formula (I):

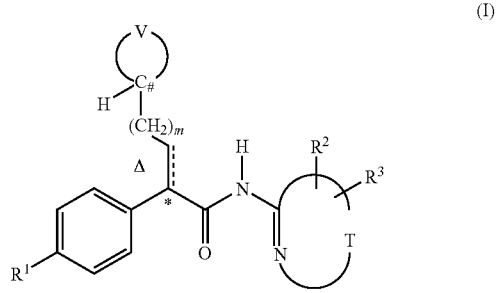

or a pharmaceutically acceptable salt thereof, wherein:

V is $(CH_2)_k$ where one $CH_2$ group is replaced by CH(OH), C=O, C=NOH, C=NOCH$_3$, CHX, CXX$^1$, CH(OCH$_3$), CH(OCOCH$_3$), CH(C$_{1-4}$alkyl), or C(OH)(C$_{1-4}$alkyl);

X and X$^1$ are independently selected from fluoro and chloro;

R$^1$ is SO$_2$R$^4$;

T together with the —N=C— to which it is attached forms a heteroaryl ring, or a heterocyclic ring where the N=C bond is the only site of unsaturation;

R$^2$ and R$^3$ each independently are hydrogen, halogen, OCF$_n$H$_{3-n}$, methoxy, CO$_2$R$^5$, cyano, nitro, CHO, CONR$^6$R$^7$, CON(OCH$_3$)CH$_3$, or C$_{1-2}$alkyl, heteroaryl, or C$_{3-7}$cycloalkyl optionally substituted with 1-5 independent halogen, hydroxy, cyano, methoxy, —NHCO$_2$CH$_3$, or —N(C$_{0-2}$alkyl)(C$_{0-2}$alkyl) substituents; or R$^2$ and R$^3$ together form a 5-8-membered aromatic, heteroaromatic, carbocyclic, or heterocyclic ring; provided that the ring formed by T together with the —N=C— to which it is attached is not 5-fluorothiazol-2-yl;

R$^4$ is a C$_{3-7}$cycloalkyl group;

R$^5$ is hydrogen, or a C$_{1-4}$alkyl group, C$_{2-4}$alkenyl group, C$_{2-4}$alkynyl group, C$_{3-7}$cycloalkyl group, aryl group, heteroaryl group, or 4-7-membered heterocyclic group, wherein any group is optionally substituted with 1-6 independent halogen, cyano, nitro, hydroxy, C$_{1-2}$alkoxy, —N(C$_{0-2}$alkyl)(C$_{0-2}$alkyl), C$_{1-2}$alkyl, C$_{3-7}$cycloalkyl, 4-7-membered heterocyclic ring, CF$_n$H$_{3-n}$, aryl, heteroaryl, CO$_2$H, —COC$_{1-2}$alkyl, —CON(C$_{0-2}$alkyl)(C$_{0-2}$alkyl), SOCH$_3$, SO$_2$CH$_3$, or —SO$_2$N(C$_{0-2}$alkyl)(C$_{0-2}$alkyl) substituents;

R$^6$ and R$^7$ each independently are hydrogen, or a C$_{1-4}$alkyl group, C$_{3-7}$cycloalkyl group, aryl group, heteroaryl group, or 4-7-membered heterocyclic group, wherein any group is optionally substituted with 1-6 independent halogen, cyano, nitro, hydroxy, C$_{1-2}$alkoxy, —N(C$_{0-2}$alkyl)(C$_{0-2}$alkyl), C$_{1-2}$alkyl, C$_{3-7}$cycloalkyl, 4-7-membered heterocyclic ring, CF$_n$H$_{3-n}$, aryl, heteroaryl, COC$_{1-2}$alkyl, —CON(C$_{0-2}$alkyl)(C$_{0-2}$alkyl), SOCH$_3$, SO$_2$CH$_3$, or —SO$_2$N(C$_{0-2}$alkyl)(C$_{0-2}$alkyl) substituents; or R$^6$ and R$^7$ together form a 6-8-membered heterobicyclic ring system or a 4-8-membered heterocyclic ring which is optionally substituted with 1-2 independent C$_{1-2}$alkyl, CH$_2$OCH$_3$, COC$_{0-2}$alkyl, hydroxy, or SO$_2$CH$_3$ substituents;

n is 1, 2 or 3;

k is an integer from 2 to 7;

m is 0 or 1; and the dotted line together with the solid line forms an optional double bond, and Δ indicates that the double bond has the (E)-configuration.

If the dotted line together with the solid line forms a single bond, the carbon atom linking the aryl ring and —HC<>V-containing sidechain to the amide carbonyl carbon, i.e. the carbon atom labelled with "*", is a chiral centre. Accordingly, at this centre, the compound may be present either as a racemate or as a single enantiomer in the (R)- or (S)-configuration. The (R)-enantiomers are preferred.

The carbon atom labelled with "#" may also be chiral. Accordingly, at this centre, the compound may be present either as a racemate or as a single enantiomer in the (R)- or (S)-configuration. The (R)-enantiomers are preferred when the dotted line together with the solid line represents a single bond. When the dotted line together with the solid line forms a double bond, the (S)-enantiomers are preferred.

In a first aspect, the present invention is directed to a compound represented by Formula (Ia):

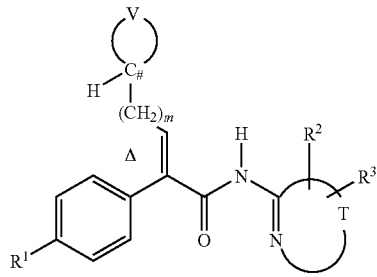

(Ia)

or a pharmaceutically acceptable salt thereof, wherein V, T, R$^1$, R$^2$, R$^3$, m and Δ are as defined above in Formula (I).

In a second and preferred aspect the invention is directed to a compound represented by Formula (Ib):

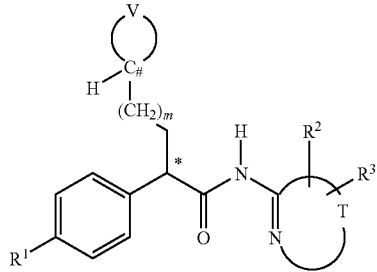

(Ib)

or a pharmaceutically acceptable salt thereof, wherein V, T, R$^1$, R$^2$, R$^3$ and m are as defined above in Formula (I).

The molecular weight of the compounds of Formula (I) is preferably less than 800, more preferably less than 600, most preferably less than 500.

In the compounds of Formula (I), the group formed by —HC< and >V preferably represents oxocycloalkyl or hydroxycycloalkyl, e.g. 3-oxocyclopentyl, 4-oxocyclohexyl or 3-hydroxycyclopentyl, particularly (R)-3-oxocyclopentyl or 4-oxocyclohexyl, more particularly (R)-3-oxocyclopentyl.

In the present invention, the ring formed by T together with the —N=C— to which it is attached is preferably a 5- or 6-membered monocyclic heteroaryl group, preferably containing one further nitrogen atom. Examples of such heteroaryl groups include pyrazole, pyrazine and pyridazine.

R$^2$ and R$^3$ are preferably independently selected from hydrogen, halogen and methyl; more preferably R$^2$ and R$^3$ are independently selected from hydrogen and methyl. Preferably one of R$^2$ and R$^3$ is hydrogen and the other is hydrogen or methyl.

Specific rings formed by T together with the —N=C— to which it is attached which may be mentioned are 1-methylpyrazol-3-yl, pyrazin-2-yl and 6-methylpyridazin-3-yl.

R$^4$ is preferably SO$_2$C$_{3-4}$cycloalkyl, especially SO$_2$cyclopropyl.

R$^5$ is preferably hydrogen or a C$_{1-4}$alkyl group.

R$^6$ and R$^7$ are preferably each independently hydrogen or a C$_{1-4}$alkyl group.

In the present invention, m is preferably 0.

In the present invention, k is preferably 4 or 5.

Specific compounds of the invention which may be mentioned are:

2(R)-2-(4-cyclopropanesulfonylphenyl)-N-(1-methylpyrazol-3-yl)-3-((R)-3-oxocyclopentyl)propionamide;

2(R)-2-(4-cyclopropanesulfonylphenyl)-N-(pyrazin-2-yl)-3-((R)-3-oxocyclopentyl)propionamide; and 2(R)-2-(4-cyclopropancsulfonylphenyl)-N-(6-methylpyridazin-3-yl)-3-((R)-3-oxocyclopentyl)propionamide;

or a pharmaceutically acceptable salt of any one thereof.

While the preferred groups for each variable have generally been listed above separately for each variable, preferred compounds of this invention include those in which several or each variable in Formula (I) is selected from the preferred, more preferred, most preferred, especially or particularly listed groups for each variable. Therefore, this invention is intended to include all combinations of preferred, more preferred, most preferred, especially and particularly listed groups.

As used herein, unless stated otherwise, "alkyl" as well as other groups having the prefix "alk" such as, for example, alkoxy, alkenyl, alkynyl, and the like, means carbon chains which may be linear or branched or combinations thereof. Examples of alkyl groups include methyl, ethyl, propyl, isopropyl, butyl, sec- and tert-butyl, and the like. "Alkenyl", "alkynyl" and other like terms include carbon chains having at least one unsaturated carbon-carbon bond.

As used herein, for example, "$C_{0-2}$alkyl" is used to mean an alkyl having 0-2 carbons—that is, 0, 1, or 2 carbons. An alkyl having no carbon is hydrogen when the alkyl is a terminal group.

The terms "cycloalkyl" and "carbocyclic ring" mean carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and the like.

The term "halogen" includes fluorine, chlorine, bromine, and iodine atoms.

The terms "aryl" and "aromatic ring" include, for example, phenyl and naphthyl, a preferred aryl group is phenyl.

Unless otherwise stated, the term "heterocyclic ring" includes 48-membered saturated rings containing one or two heteroatoms chosen from oxygen, sulfur, and nitrogen. The heteroatoms are not directly attached to one another. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,3]dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

Unless otherwise stated, the terms "heteroaryl" and "heteroaromatic ring" include 5- or 6-membered heteroaryl rings containing 1-4 heteroatoms chosen from oxygen, sulfur, and nitrogen. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, and triazinyl.

The above formulae are shown without a definitive stereochemistry at certain positions. The present invention includes all stereoisomers (e.g. geometric isomers, optical isomers, diastercoisomers, etc.) and pharmaceutically acceptable salts thereof, except where specifically drawn or stated otherwise. Further, mixtures of stereoisomers as well as isolated specific stereoisomers are also included, except where specifically drawn or stated otherwise. During the course of the synthetic procedures used to prepare such compounds, or in using racemization or epimerization procedures known to those skilled in the art, the products of such procedures can be a mixture of stereoisomers. When a tautomer of the compound of the above formulae exists, the present invention includes any possible tautomers and pharmaceutically acceptable salts thereof, and mixtures thereof, except where specifically drawn or stated otherwise. When the compound of the above formulae and pharmaceutically acceptable salts thereof exist in the form of solvates or polymorphic forms, the present invention includes any possible solvates and polymorphic forms. The type of a solvent that forms the solvate is not particularly limited so long as the solvent is pharmacologically acceptable. For example, water, ethanol, propanol, acetone or the like can be used.

Since the compounds of Formula (I) are intended for pharmaceutical use they are preferably provided in substantially pure form, for example at least 60% pure, more suitably at least 75% pure, at least 95% pure and especially at least 98% pure (% are on a weight for weight basis).

The invention also encompasses a pharmaceutical composition that is comprised of a compound of Formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of Formula (I), or a pharmaceutically acceptable salt thereof.

Moreover, within this embodiment, the invention encompasses a pharmaceutical composition for the prophylaxis or treatment of hyperglycemia and diabetes, particularly type II diabetes, by the activation of GK, comprising a pharmaceutically acceptable carrier and a non-toxic therapeutically effective amount of compound of Formula (I), or a pharmaceutically acceptable salt thereof.

The invention also provides the use of a compound of Formula (I), or a pharmaceutically acceptable salt thereof, as a pharmaceutical.

The compounds and compositions of the present invention are effective for treating hyperglycemia and diabetes, particularly type II diabetes, in mammals such as, for example, humans.

The invention also provides a method of prophylactic or therapeutic treatment of a condition where activation of GK is desirable comprising a step of administering an effective amount of a compound of Formula (I), or a pharmaceutically acceptable salt thereof.

The invention also provides a method of prophylactic or therapeutic treatment of hyperglycemia or diabetes, particularly type II diabetes, comprising a step of administering an effective amount of a compound of Formula (I), or a pharmaceutically acceptable salt thereof.

The invention also provides a method for the prevention of diabetes, particularly type II diabetes, in a human demonstrating pre-diabetic hyperglycemia or impaired glucose tolerance comprising a step of administering an effective prophylactic amount of a compound of Formula (I), or a pharmaceutically acceptable salt thereof.

The invention also provides the use of a compound of Formula (I), or a pharmaceutically acceptable salt thereof, as a GK activator.

The invention also provides the use of a compound of Formula (I), or a pharmaceutically acceptable salt thereof, for the prophylactic or therapeutic treatment of hyperglycemia or diabetes, particularly type II diabetes.

The invention also provides the use of a compound of Formula (I), or a pharmaceutically acceptable salt thereof, for the prevention of diabetes, particularly type II diabetes, in a human demonstrating pre-diabetic hyperglycemia or impaired glucose tolerance.

The invention also provides the use of a compound of Formula (I), or a pharmaceutically acceptable salt thereof, in the manufacture of a medicament for the activation of GK.

The invention also provides the use of a compound of Formula (I), or a pharmaceutically acceptable salt thereof, in the manufacture of a medicament for the prophylactic or therapeutic treatment of hyperglycemia or diabetes, particularly type II diabetes.

The invention also provides the use of a compound of Formula (I), or a pharmaceutically acceptable salt thereof, in the manufacture of a medicament for the prevention of diabetes, particularly type II diabetes, in a human demonstrating pre-diabetic hyperglycemia or impaired glucose tolerance.

The compounds and compositions of the present invention may be optionally employed in combination with one or more other anti-diabetic agents or anti-hyperglycemic agents, which include, for example, sulfonylureas (e.g. glyburide, glimepiride, glipyride, glipizide, chlorpropamide, gliclazide, glisoxepid, acetohexamide, glibornuride, tolbutamide, tolazamide, carbutamide, gliquidone, glybexamide, phenbutamide, tolcyclamide, etc.), biguanides (e.g. metformin, phenformin, buformin, etc.), glucagon antagonists (e.g. a peptide or non-peptide glucagon antagonist), glucosidase inhibitors (e.g. acarbose, miglitol, etc.), insulin secetagouges, insulin sensitizers (e.g. troglitazone, rosiglitazone, pioglitazone, etc.) and the like; or anti-obesity agents (e.g. sibutramine, orlistat, etc.) and the like. The compounds and compositions of the present invention and the other anti-diabetic agents or anti-hyperglycemic agents may be administered simultaneously, sequentially or separately.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthetic amines. Other pharmaceutically acceptable organic non-toxic bases from which salts can be formed include, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salts can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, methanesulfonic, and tartaric acids.

The pharmaceutical compositions of the present invention comprise a compound of Formula (I), or a pharmaceutically acceptable salt thereof, as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, as well as administration through inhaling, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The pharmaceutical compositions according to the invention are preferably adapted for oral administration.

In practice, the compounds of Formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compounds of Formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound of Formula (I), or a pharmaceutically acceptable salt thereof. The compounds of Formula (I), or pharmaceutically acceptable salts thereof, can also be included in pharmaceutical compositions in combination with one or more other therapeutically active compounds.

The pharmaceutical compositions of this invention include pharmaceutically acceptable liposomal formulations containing a compound of Formula (I), or a pharmaceutically acceptable salt thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules, and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin, or acacia; and lubricating agents, for example, magnesium stearate, stearic acid, or talc. The tablets may be uncoated or they may be coated by known techniques to delay disintegration and absorption in the gastrointestinal tract and thereby provide a sustained action over a longer time. For example, a time delay material such as glyceryl monostearate, or glyceryl distearate may be used.

In hard gelatin capsules, the active ingredient is mixed with an inert solid diluent, for example, calcium carbonate, calcium phosphate, or kaolin. In soft gelatin capsules, the active ingredient is mixed with water or an oil medium, for example, peanut oil, liquid paraffin, or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95% of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage and thus, preferably should be preserved against the contaminating action of microorganisms such as bacteria and fungi. The carrier can be a solvent or dispersion medium containing, for example, water, ethanol, polyol (e.g. glycerol, propylene glycol, and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound of Formula (I), or a pharmaceutically acceptable salt thereof, via conventional processing methods. As an example, a cream or ointment is prepared by admixing hydrophilic material and water, together with about 5 wt % to about 10 wt % of the compound of Formula (I), to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

Pharmaceutical compositions of this invention can be in a form suitable for inhaled administration. Such administration can be in forms and utilizing carriers described in, for example, 1) Particulate Interactions in Dry Powder Formulations for Inhalation, Xian Bang et al, 2000, Taylor and Francis, 2) Pharmaceutical Inhalation Aerosol Technology, Anthony Hickey, 1992, Marcel Dekker, 3) Respiratory Drug Delivery, 1990, Editor: P. R. Byron, CRC Press.

In addition to the aforementioned carrier ingredients, the pharmaceutical compositions described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of Formula (I), or a pharmaceutically acceptable salt thereof, may also be prepared in powder or liquid concentrate form.

Generally, dosage levels of the order of from about 0.01 mg/kg to about 150 mg/kg of body weight per day are useful in the treatment of the above-indicated conditions, or alternatively about 0.5 mg to about 10 g per patient per day. For example, type II diabetes may be effectively treated by the administration of from about 0.01 to 100 mg of the compound per kilogram of body weight per day, or alternatively about 0.5 mg to about 7 g per patient per day.

It is understood, however, that the specific dose level for any particular patient will depend upon a variety of factors including the age, body weight, general health, sex, diet, time of administration, route of administration, rate of excretion, drug combination and the severity of the disease in the particular diabetic patient undergoing therapy. Further, it is understood that the compounds and salts thereof of this invention can be administered at sub-therapeutic levels prophylactically in anticipation of a hyperglycemic condition.

The compounds of Formula (I) may exhibit advantageous properties compared to known glucokinase activators, such properties may be illustrated in the assays described herein or in other assays known to those skilled in the art. In particular, compounds of the invention may exhibit improved values for $K_m$, $V_{max}$, $EC_{50}$, maximum activation (glucose concentration=5 mM), maximum blood glucose reduction on basal blood glucose levels and/or reduction of postprandial glucose peak in an oral glucose tolerance test (OGTT), or other advantageous pharmacological properties such as enhanced aqueous solubility, reduced plasma protein binding and/or enhanced metabolic stability, compared to known GK activators.

EXPERIMENTAL

In accordance with this invention, the compounds of Formula (Ia) can be prepared following the protocol illustrated in Scheme 1 below:

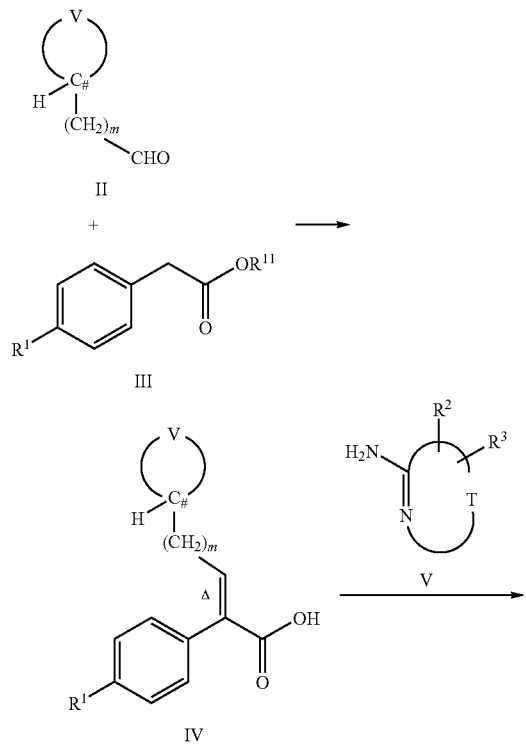

wherein V, T, $R^1$, $R^2$, $R^3$, m and Δ are as described above, and $R^{11}$ is $C_{1-4}$alkyl. The aldehydes II and phenylacetic esters III are commercially available or are readily prepared using known techniques. The α-carbanion of the phenylacetic ester III ($R^{11}=C_{1-4}$alkyl), generated at −78° C. in, for example, tetrahydrofuran, by a strong base, e.g. lithium diisopropylamide, may be condensed with II to give an α,β-unsaturated ester (T. Severin et al. *Chem. Ber.,* 1985, 118, 4760-4773) that may be saponified using, for example, sodium hydroxide (W. L. Corbett et al., WO 01/44216), to produce IV. If necessary, any functional groups within the intermediate compounds, e.g. oxo or hydroxy groups in the compounds of formula II, may be protected and the protecting groups removed using conventional means. For example oxo groups may be protected as ketals and hydroxy groups as ethers, e.g. methoxymethyl (MOM) ethers.

The α,β-unsaturated carboxylic acids IV may be condensed with the amine V, or a salt thereof e.g. the hydrochloride salt, using a variety of coupling conditions, e.g. polymer supported carbodiimide-1-hydroxybenzotriazole in N,N-dimethylformamide at 20° C. (for representative procedures, see http://www.argotech.com/PDF/resins/ps_carbodiimide.pdf and available from Argonaut Technologies, Inc., Foster City, Calif.), to give (Ia).

In accordance with this invention, the compounds of Formula (Ib) can be prepared following the protocol illustrated in Scheme 2 below:

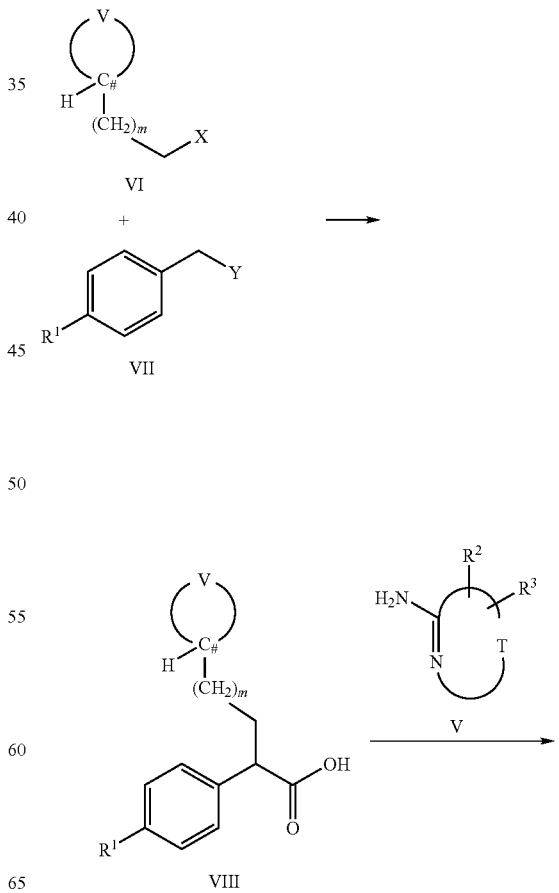

-continued

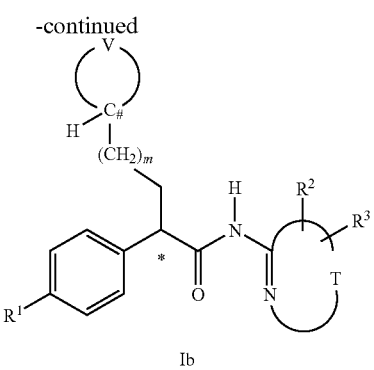

Ib wherein V, T, R¹, R², R³ and m are as described above, Y is $CO_2R^{12}$ wherein $R^{12}$ is hydrogen, $C_{1-4}$alkyl or benzyl; and X is chloro, bromo, iodo, or —$OSO_2R^{13}$, wherein $R^{13}$ is $C_{1-4}$alkyl, optionally substituted with one or more fluorines, or optionally substituted aryl.

The halides and sulfonate esters VI and the phenylacetic acids and esters VII are commercially available or are readily prepared using known techniques, for example as described in International Patent Publication Nos. WO2000/058293, WO2001/044216 and WO2003/095438. These alkylating agents may be reacted with the dianions of the phenylacetic acids VII, generated at −78° C. in tetrahydrofuran with ≧2 equivalents of a strong base, such as lithium diisopropylamide, to generate VIII directly (F. T. Bizzarro et al., WO2000/58293). Alternatively, the x-carbanion of phenylacetic ester VII, generated at −78° C. in tetrahydrofuran by a strong base, such as lithium bis(trimethylsilyl)amide (L. Snyder et al., *J. Org. Chem.*, 1994, 59, 7033-7037), can be alkylated by VI to give α-substituted esters. Saponification of these esters, employing, for example, sodium hydroxide in aqueous methanol at 20° C. to reflux, leads to the carboxylic acids VIII. If necessary, any functional groups within the intermediate compounds, e.g. oxo or hydroxy groups in the compounds of formula VI, may be protected and the protecting groups removed using conventional means. For example oxo groups may be protected as ketals and hydroxy groups as ethers, e.g. methoxymethyl (MOM) ethers.

The carboxylic acids VIII may be condensed with the amine V, or a salt thereof e.g. the hydrochloride salt, using a variety of coupling conditions, e.g. polymer supported carbodiimide-1-hydroxybenzotriazole in N,N-dimethylformamide at 20° C. (for representative procedures, see http://www.argotech.com/PDF/resins/ps_carbodiimide.pdf and available from Argonaut Technologies, Inc., Foster City, Calif.), to give amides (Ib).

The compound of Formula (Ib) has an asymmetric carbon atom which interlinks the amide carbonyl carbon, the aryl ring, and the —HC< >V containing sidechain. In accordance with this invention, the preferred stereoconfiguration at the asymmetric centre is (R).

If one desires to isolate the pure (R)- or (S)-stereoisomers of the compound of Formula (Ib), it is possible to resolve a racemic mixture of the chiral carboxylic acid precursor VIII by any conventional chemical means and then condense the enantiopure carboxylic acids with amine V, or a salt thereof, using a reagent that causes negligible racemisation. By way of illustration, racemic VIII can be condensed with a chiral oxazolidinone derivative (see, for instance, F. T. Bizzarro et al., WO2000/58293) to generate a mixture of diastereoisomeric imides that are separable by any conventional method, e.g. column chromatography. Hydrolysis of the pure imides affords the stereopure (R)- and (S)-carboxylic acids that can then be condensed with amine V, or a salt thereof, employing a reagent that minimises racemisation of the chiral centre, e.g. benzotriazol-1-yloxytris(pyrrolidino)phosphonium hexafluorophosphate (J. Coste et al., *Tetrahedron Let.*, 1990, 31, 205-208), to furnish enantiopure (R)- or (S)-amides of Formula (Ib). Alternatively, a racemic mixture of amides of Formula (Ib) can be separated by means of chiral high performance liquid chromatography employing a chiral stationary phase which can be purchased from, for example, Daicel Chemical Industries, Ltd, Tokyo, Japan.

Various functional groups present in the compounds of Formula (I) and intermediates for use in the preparation thereof may be produced by functional group conversions known to those skilled in the art. For example in the compounds of formula VIII sulfonyl groups may be produced by oxidation of the corresponding sulfanyl group using e.g. mCPBA.

Further details for the preparation of the compounds of Formula (I) are found in the examples.

The compounds of Formula (I) may be prepared singly or as compound libraries comprising at least 2, for example 5 to 1,000, compounds and more preferably 10 to 100 compounds of Formula (I). Compound libraries may be prepared by a combinatorial "split and mix" approach or by multiple parallel synthesis using either solution or solid phase chemistry, using procedures known to those skilled in the art.

During the synthesis of the compounds of Formula (I), labile functional groups in the intermediate compounds, e.g. hydroxy, oxo, carboxy and amino groups, may be protected. The protecting groups may be removed at any stage in the synthesis of the compounds of Formula (I) or may be present on the final compound of Formula (X). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, $2^{nd}$ edition.

Any novel intermediates as defined above are also included within the scope of the invention. Thus the invention also provides a compound of Formula (IV) or (VIII), or a protected derivative or salt thereof, as defined above.

All publications, including, but not limited to, patents and patent application cited in this specification, are herein incorporated by reference as if each individual publication were specifically and individually indicated to be incorporated by reference herein as fully set forth.

Materials and Methods

Column chromatography may be carried out on $SiO_2$ (40-63 mesh) unless specified otherwise. LCMS data may be obtained employing one of two methods: Method A: Waters Symmetry 3.5μ $C_{18}$ column (2.1×30.0 mm, flow rate=0.8 mL/min) eluting with a (5% MeCN in $H_2O$)-MeCN solution containing 0.1% $HCO_2H$ over 6 min and UV detection at 220 nm. Gradient information: 0.0-1.2 min: 100% (5% MeCN in $H_2O$); 1.2-3.8 min: Ramp up to 10% (5% MeCN in $H_2O$)-90% MeCN; 3.8-4.4 min: Hold at 10% (5% MeCN in $H_2O$)-90% MeCN; 4.4-5.5 min: Ramp up to 100% MeCN; 5.5-6.0 min: Return to 100% (5% MeCN in $H_2O$). Method B: Phenomenex Mercury Luna 3μ $C_{18}$ column (2.0×10.0 mm, flow rate=1.5 mL/min), eluting with a (5% MeCN in $H_2O$)-MeCN solution (4:1 to 1:4) containing 0.1% $HCO_2H$ over 2.95 min, & employing diode array detection. The mass spectra for both Methods A and B may be obtained employing an electrospray ionisation source in either the positive ($ES^+$) ion or negative ion (ES⁻) mode. Atmospheric Pressure Chemical Ionisation (APCI) spectra may be obtained on a FinniganMat SSQ 7000C instrument.

The synthesis of the following compound has been reported previously:
7(S)-iodomethyl-2(S),3(S)-diphenyl-1,4-dioxaspiro[4,4]nonane: WO2003/095438.

Abbreviations and acronyms: Ac: Acetyl; ATP: Adenosine 5'-triphosphate; DMF: N,N-Dimethylformamide; DMPU: 1,3-Dimethyl-3,4,5,6-tetrahydro-2(1H)-pyrimidinone; DMSO: Dimethylsulfoxide; Et: Ethyl; FA: Fold activation; GK: Glucokinase; Glc: Glucose; G6P: Glucose-6-phosphate; G6PDH: Glucose-6-phosphate dehydrogenase; GST-GK: Glutathione S-transferase-Glucokinase fusion protein; IH: Isohexane; LHMDS: Lithium bis(trimethylsilyl)amide; NADP(H): β-Nicotinamide adenine dinucleotide phosphate (reduced); RT: Retention time; THF: Tetrahydrofuran.

Preparation 1

(4-Cyclopropylsulfanylphenyl)oxoacetic acid

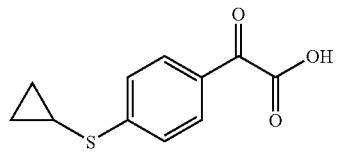

2M aqueous NaOH (163 ml) was added to a solution of ethyl (4-cyclopropylsulfanylphenyl)oxoacetate (40.62 g, 162.5 mmol) in EtOH (200 ml) and the stirred mixture heated at 60° C. for 2 h. After cooling, the mixture was concentrated to 150 ml and washed with ether (2×100 ml). Sufficient concentrated HCl was then added to adjust the pH to 1 and the resulting precipitate was extracted into EtOAc (2×300 ml). The combined organic phases were washed with water (3×100 ml), brine (200 ml) and dried (MgSO₄). Removal of the solvent afforded the title compound: m/z (ES⁻)=221.0 [M−H⁺]⁻.

Preparation 2

(4-Cyclopropylsulfanylphenyl)acetic acid

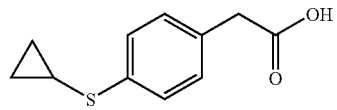

Hydrazine hydrate (14.19 g, 283.5 mmol) was cooled to −50° C. and (4-cyclopropylsulfanylphenyl)oxoacetic acid (Preparation 1, 12.6 g, 56.7 mmol) added in one portion. The vigorously-stirred slurry was warmed firstly to room temperature and then at 80° C. for 5 min. Solid KOH (8.76 g, 156.5 mmol) was added in four equal portions and the resulting solution heated at 100° C. for 20 h. On cooling to room temperature, water (25 ml) was added and the aqueous phase washed with Et₂O (20 ml). The ethereal phase was itself washed with water (2×15 ml) and sufficient concentrated HCl added to the combined aqueous phases to adjust the pH to 1. The resulting precipitate was then extracted into EtOAc (2×300 ml) and the combined organic phases washed with water (3×100 ml), brine (200 ml) then dried (MgSO₄). Evaporation of the solvent afforded the title compound: m/z (ES⁻)= 207.1 [M−H⁺]⁻.

Preparation 3

2-(4-Cyclopropylsulfanylphenyl)-N-(2(R)-hydroxy-1(R)-methyl-2-phenylethyl)-N-methylacetamide

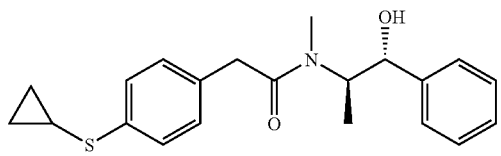

Anhydrous acetone (148 ml) was added to (4-cyclopropylsulfanylphenyl)acetic acid (Preparation 2, 16.41 g, 78.8 mmol) and K₂CO₃ (32.67 g, 236.4 mmol) to form a slurry which was cooled to −10° C. with stirring. Neat trimethylacetyl chloride (10.2 ml, 82.74 mmol) was introduced dropwise, ensuring the temperature did not exceed −10° C. during the addition. The reaction mixture was stirred at −10° C. for 20 min, warmed to 0° C. for 20 min then cooled to −15° C. and solid (1(R),2(R))-(−)-pseudoephedrine (19.53 g, 118.2 mmol) was added in one portion. After 10 min, the reaction mixture was brought to room temperature, where stirring was continued for 1.5 h. Water (100 ml) was added and the mixture extracted with EtOAc (500 ml). The organic phase was washed with water (2×100 ml) and the combined aqueous layers back-extracted with EtOAc (2×250 ml). The combined organic layers were then washed with brine (100 ml) and dried (MgSO₄). The solvent was removed and the solid yellow residue recrystallized from EtOAc—IH to afford the title compound: m/z (ES⁺)=356.1 [M+H]⁺.

Preparation 4

2(R)-(4-Cyclopropylsulfanylphenyl)-3-(3(R)-oxocyclopentyl)propionic acid

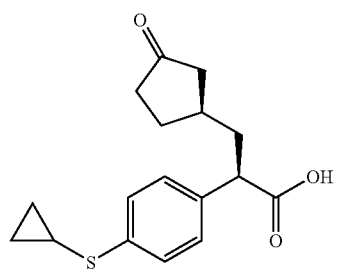

LHMDS (162 ml of a 1M solution in THF, 162 mmol) was diluted with anhydrous THF (161 ml) and cooled to −20° C. with stirring. A solution of 2-(4-cyclopropylsulfanylphenyl)-N-(2(R)-hydroxy-1(R)-methyl-2-phenylethyl)-N-methylacetamide (Preparation 3, 30 g, 84.4 mmol) in anhydrous THF (245 ml) was added via cannula over 10 min, ensuring the reaction temperature remained below −15° C. throughout the addition. The reaction was allowed to warm to −7° C. over 30 min then cooled to −12° C. and a solution of 7(S)-iodomethyl-2(S),3(S)-diphenyl-1,4-dioxaspiro[4,4]nonane (27 g, 64.2 mmol) in a mixture of anhydrous THF (111 ml) and DMPU (18.9 ml) added via cannula over 10 min, ensuring the reaction temperature remained below −7° C. throughout. The reaction was warmed to 2° C. and stirred for 4.5 h before being poured into a mixture of toluene (770 ml) and 20% aqueous NH₄Cl (550 ml). After stirring vigorously, the organic layer was separated and washed with 20% aqueous NH$_4$Cl (550 ml) and brine (100 ml). The aqueous phases were combined and extracted with EtOAc (500 ml) which, after separation, was washed with brine (100 ml). The combined organic phases were dried (MgSO$_4$), filtered, evaporated and the resulting oil purified by flash chromatography (1H-EtOAc, 9:1 changing incrementally to 1:1) to afford 2(R)-(4-cyclopropylsulfanylphenyl)-3-(2(S),3(S)-diphenyl-1,4-dioxaspiro[4.4]non-7(R)-yl)-N-(2(R)-hydroxy-1(R)-methyl-2-phenylethyl)-N-methylpropionamide: m/z (ES$^+$)=648.3 [M+H]$^+$. A stirred solution of this amide (30.7 g, 47.38 mmol) in 1,4-dioxane (62 ml) was diluted with 4.5M aqueous H$_2$SO$_4$ (61.5 ml) and the resulting mixture heated under gentle reflux for 18 h. After cooling on ice, water (162 ml) was added and the mixture extracted with EtOAc (250 ml). The aqueous layer was separated and extracted further with EtOAc (2×150 ml) and the combined organic phases washed with water (3×200 ml), ensuring the final wash was pH neutral, and brine (100 ml). After drying (MgSO$_4$) and filtering, the solvent was removed and the residue purified by flash chromatography (CH$_2$Cl$_2$ then CH$_2$Cl$_2$-THF, 5:1 changing to 3:1) to afford the title compound: m/z (ES$^+$)=305.1 [M+H]$^+$.

Preparation 5

2(R)-(4-Cyclopropanesulfonylphenyl)-3-(3(R)-oxocyclopentyl)propionic acid

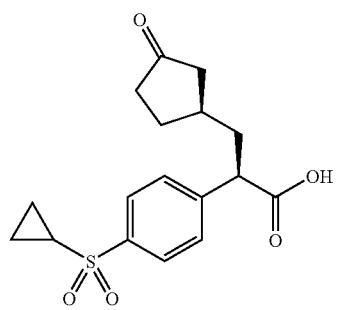

A stirred solution of 2(R)-(4-cyclopropylsulfanylphenyl)-3-(3(R)-oxocyclopentyl)propionic acid (Preparation 4, 5.0 g, 16.43 mmol) in CH$_2$Cl$_2$ (250 ml) was cooled to 1° C. on ice and 70% mCPBA (8.099 g, 32.85 mmol) added portionwise, maintaining the temperature below 3° C. After 6 h the solvent was removed and the residue purified by flash chromatography (1% AcOH in CH$_2$Cl$_2$ then THF) to afford the title compound: m/z (ES$^-$)=337.1 [M+H]$^+$.

Example 1

2(R)-(4-Cyclopropanesulfonylphenyl)-3-(3(R)-oxocyclopentyl)-N-pyrazin-2-ylpropionamide

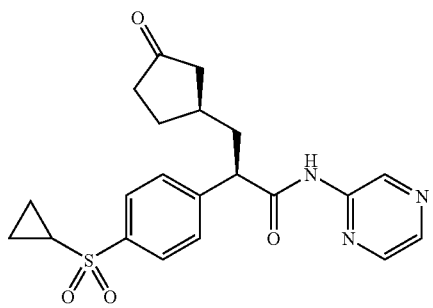

A solution of 2(R)-(4-cyclopropanesulfonylphenyl)-3-(3(R)-oxocyclopentyl)-propionic acid (Preparation 5, 250 mg, 0.743 mmol) in anhydrous CH$_2$Cl$_2$ (10 ml) was cooled to 0° C. and a solution of oxalyl chloride (0.114 g, 0.899 mmol) in anhydrous CH$_2$Cl$_2$ (2 ml) added dropwise, maintaining the temperature at 0° C. during the addition. Dry DMF (0.05 ml) was added and the reaction mixture stirred for 2.5 h. Solid 2-aminopyrazine (78 mg, 0.82 mmol) was added quickly in one portion, followed by pyridine (0.12 ml, 1.45 mmol) and the mixture stirred at 0° C. for 2 h then at room temperature overnight. The solution was diluted with EtOAc (60 ml) and washed with aqueous 5% w/v citric acid (2×20 ml), saturated aqueous NaHCO$_3$ (2×20 ml), water (20 ml) and brine (20 ml). The organic phase was dried (MgSO$_4$), evaporated and the residue purified by flash chromatography (1H-EtOAc, 1:4) to afford the title compound: RT=3.14 min; m/z (ES$^+$)=414.2 [M+H]$^+$.

The amides in Table I were prepared using a similar method to that described in Example 1.

TABLE I

| Example | Structure | Name | RT (min) | m/z (ES$^+$) |
|---|---|---|---|---|
| 2 | 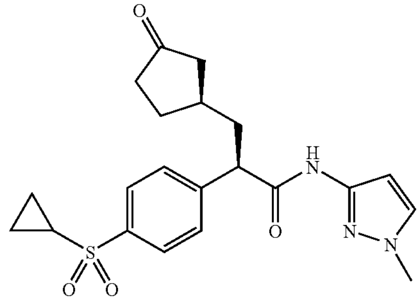 | 2(R)-(4-Cyclopropanesulfonylphenyl)-N-(1-methyl-1H-pyrazol-3-yl)-3-(3(R)-oxocyclopentyl)-propionamide | 3.11 | 416.2 [M + H]$^+$ |

TABLE I-continued

| Example | Structure | Name | RT (min) | m/z (ES⁺) |
|---|---|---|---|---|
| 3 | 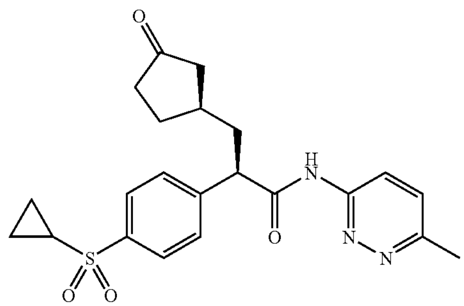 | 2(R)-(4-Cyclopropane-sulfonylphenyl)-N-(6-methylpyridazin-3-yl)-3-(3(R)-oxocyclopentyl)-propionamide | 3.15 | 428.2 [M + H]⁺ |

Assays

In Vitro GK Activity

Using a protocol similar to that described in WO2000/58293, GK activity may be assayed by coupling the production of G6P by GST-GK to the generation of NADPH with G6PDH as the coupling enzyme.

The GK assay is performed at 30° C. in a flat bottom 96-well assay plate from Costar with a final incubation volume of 100 µL. The assay buffer contains: 25 mM Hepes buffer (pH 7.4), 12.5 mM KCl, 5 mM D-Glc, 5 mM ATP, 6.25 mM NADP, 25 mM $MgCl_2$, 1 mM dithiothreitol, test compound or 5% DMSO, 3.0 unit/mL G6PDH, and 0.4 µL/mL GST-GK, derived from human liver GK. ATP, G6PDH, and NADP may be purchased from Roche Diagnostics. The other reagents are >98% pure and may be purchased from Kanto Chemicals. The test compounds are dissolved in DMSO, before being added to the assay buffer without ATP. This mix is preincubated in the temperature controlled chamber of a SPECTRAmax 250 microplate spectrophotometer (Molecular Devices Corporation, Sunnyvale, Calif.) for 10 min, then the reaction started by the addition of 10 µL ATP solution.

After starting the reaction, the increase in optical density (OD) at 340 nm is monitored over a 10 min incubation period as a measure of GK activity. Sufficient GST-GK is added to produce an increase in $OD_{340}$ over the 10 min incubation period in wells containing 5% DMSO, but no test compound. Preliminary experiments have established that the GK reaction is linear over this period of time, even in the presence of activators that produced a 8-fold increase in GK activity. The GK activity in control wells is compared with the activity in wells containing test GK activators. The compound concentrations that produced a 50% increase in GK activity (i.e. FA1.5) are calculated. GK activators achieve FA1.5 at ≦30 µM.

In Vivo GK Activity (I)

Following an 18 h fasting period, C57BL/6J mice are dosed orally via gavage with GK activator at 50 mg/kg body weight. Blood Glc determinations are made 5 times during the 6 h post-dose study period.

Mice (n=5) are weighed and fasted for 18 h before oral treatment. GK activators are dissolved in the Gelucire vehicle reported in WO2000/58293 (EtOH:Gelucirc44/14:PEG400q.s. 4:66:30 v/v/v) at a concentration of 13.3 mg/mL. Mice are dosed orally with 7.5 mL formulation per kg of body weight to equal a 50 mg/kg dose. Immediately prior to dosing, a pro-dose (time zero) blood Glc reading is acquired by snipping off a small portion of the animals' tails (<1 mm) and collecting 15 µL blood for analysis. After GK activator treatment, further blood Glc readings are taken at 1, 2, 4, and 6 h post-dose from the same tail wound. Results are interpreted by comparing the mean blood Glc values of 5 vehicle treated mice with the 5 GK activator treated mice over the 6 h study duration. Compounds are considered active when they exhibit a statistically significant decrease in blood Glc compared to vehicle for 2 consecutive assay time points.

In Vivo GK Activity (II)

The antihyperglycaemic effects of examples of the GK activators of the invention were evaluated in an oral glucose tolerance test in 7-8 week old male C57B1/6 ob/ob mice. Briefly, mice (n=6) were weighed and their basal blood glucose levels determined from 20 µL of blood withdrawn from a tail cut (T−27 h). After 22 h (T−5 h), food was removed and the mice were placed in fresh cages with access to water ad libitum. The blood glucose levels were determined at T−0.75 h from 20 µL of blood withdrawn from the tail wound. The GK activators were dissolved in a Gelucire 44/14-water (1:9 v/v) mixture at a concentration of 0.5 mg/mL, then, at T−0.5 h, the mice were dosed orally with 10 mL formulation per kg of body weight to equal a 5 mg/kg dose. At T=0 h, the mice were bled (20 µL) for analysis of blood glucose levels, then immediately dosed orally with glucose (2 g/kg). Further blood samples (20 µL) were taken from each animal at T=+0.5, +1.0, +1.5, +2.0, +3.0, and +4.0 h for the analysis of glucose levels. Representative GK activators of the invention reduced the area under the glucose curve by at least 20% in the 2 h following administration of glucose.

What is claimed is:

1. A compound of Formula (I):

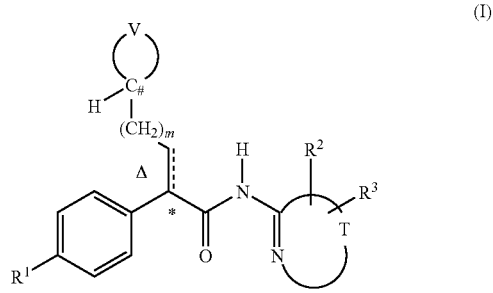

or a pharmaceutically acceptable salt thereof, wherein:

21

V is $(CH_2)_k$; where one $CH_2$ group is replaced by CH(OH) or C=O;

$R^1$ is $SO_2R^4$;

T together with the —N=C— represents pyrazolyl, pyrazinyl or pyridazinyl;

$R^2$ and $R^3$ each independently are hydrogen, halogen, $OCF_nH_{3-n}$, methoxy, $CO_2R^5$, cyano, nitro, CHO, $CONR^6R^7$, $CON(OCH_3)CH_3$, or $C_{1-2}$alkyl;

$R^4$ is a $C_{3-7}$cycloalkyl group;

$R^5$ is hydrogen, or a $C_{1-4}$alkyl group;

$R^6$ and $R^7$ each independently are hydrogen or a $C_{1-4}$alkyl group;

n is 1, 2 or 3;

k is 4 or 5;

m is 0 or 1; and the dotted line together with the solid line forms an optional double bond, and Δ indicates that the double bond has the (E)-configuration.

2. A compound according to claim 1, or a pharmaceutically acceptable salt thereof, wherein the dotted line together with the solid line forms a single bond.

3. A compound according to claim 2, or a pharmaceutically acceptable salt thereof, wherein the dotted line together with the solid line forms a single bond, and the absolute configuration at the asymmetric centre a to the amide carbonyl carbon is (R).

4. A compound according to claim 1, or a pharmaceutically acceptable salt thereof, wherein m is 0.

5. A compound according to claim 1, or a pharmaceutically acceptable salt thereof, wherein the group formed by

is 3-oxocyclopentyl, 4-oxocyclohexyl or 3-hydroxycyclopentyl.

6. A compound according to claim 5, or a pharmaceutically acceptable salt thereof, wherein the group formed by

is 3-oxocyclopentyl.

7. A compound according to claim 1, or a pharmaceutically acceptable salt thereof, wherein $R^4$ is $C_{3-4}$cycloalkyl.

8. A compound according to claim 1, or a pharmaceutically acceptable salt thereof, wherein $R^2$ and $R^3$ are independently selected from hydrogen, halogen and methyl.

9. A compound according to claim 1, or a pharmaceutically acceptable salt thereof, wherein the ring formed by T together with the —N=C— to which it is attached is selected from 1-methylpyrazol-3-yl, pyrazin-2-yl and 6-methylpyridazin-3-yl.

10. A compound according to claim 1 selected from:

2(R)-2-(4-cyclopropanesulfonylphenyl)-N-(1-methylpyrazol-3-yl)-3-((R)-3-oxocyclopentyl)propionamide;

2(R)-2-(4-cyclopropanesulfonylphenyl)-N-(pyrazin-2-yl)-3-((R)-3-oxocyclopentyl)propionamide; and

22

2(R)-2-(4-cyclopropanesulfonylphenyl)-N-(6-methylpyridazin-3-yl)-3-((R)-3-oxocyclopentyl)propionamide;

or a pharmaceutically acceptable salt of any one thereof.

11. A pharmaceutical composition comprising a compound according to claim 1, or a pharmaceutically acceptable salt thereof, and a pharmaceutically acceptable carrier.

12. A process for the preparation of a compound of Formula (I):

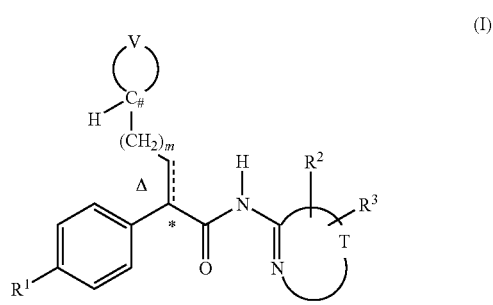

or a pharmaceutically acceptable salt thereof, said process comprising the condensation of a compound of the formula immediately below:

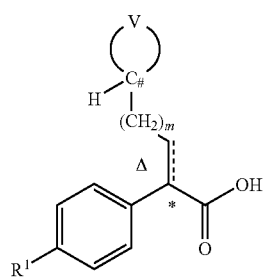

with a compound of Formula (V):

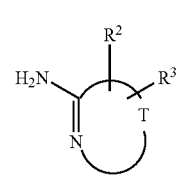

or a salt thereof, wherein the dotted line together with solid line forms an optional double bond, and V, T, $R^1$, $R^2$, $R^3$, m and Δ are as defined in claim 1.

13. A compound according to claim 8, or a pharmaceutically acceptable salt thereof, wherein the ring formed by T together with the —N=C— to which it is attached is selected from 1-methylpyrazol-3-yl, pyrazin-2-yl and 6-methylpyridazin-3-yl.

14. A compound of a formula illustrated below:

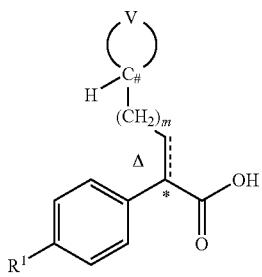

or a salt thereof, wherein V, R¹, and m are as defined in claim 1, the dotted line together with the solid line forms an optional double bond, and Δ indicates that the double bond has the (E) configuration.

15. A compound according to claim 14 wherein the dotted line together with the solid line forms a double bond.

16. A compound according to claim 14 wherein the dotted line together with the solid line forms a single bond.

17. The process according to claim 12 wherein the dotted line together with the solid line forms a double bond.

18. The process according to claim 12 wherein the dotted line together with the solid line forms a single bond.

* * * * *